US012649818B2

(12) United States Patent
Pai et al.

(10) Patent No.: US 12,649,818 B2
(45) Date of Patent: Jun. 9, 2026

(54) XYLYLENE DIISOCYANATE COMPOSITION AND OPTICAL COMPOSITION COMPRISING SAME

(71) Applicant: SK pucore co., ltd., Ulsan (KR)

(72) Inventors: Jae Young Pai, Gyeonggi-do (KR); Jung Hwan Myung, Gyeonggi-do (KR); Hyuk Hee Han, Gyeonggi-do (KR); Kyeong Hwan You, Gyeonggi-do (KR); Jeong Moo Kim, Gyeonggi-do (KR); Eui Jun Choi, Gyeonggi-do (KR); Jung Hwan Shin, Gyeonggi-do (KR)

(73) Assignee: SK PUCORE CO., LTD., Ulsan (KR)

( * ) Notice: Subject to any disclaimer, the term of this patent is extended or adjusted under 35 U.S.C. 154(b) by 450 days.

(21) Appl. No.: 18/254,172

(22) PCT Filed: Nov. 30, 2021

(86) PCT No.: PCT/KR2021/017850

§ 371 (c)(1),
(2) Date: May 24, 2023

(87) PCT Pub. No.: WO2022/119271

PCT Pub. Date: Jun. 9, 2022

(65) Prior Publication Data

US 2024/0026063 A1 Jan. 25, 2024

(30) Foreign Application Priority Data

Dec. 3, 2020 (KR) ........................ 10-2020-0167728

(51) Int. Cl.

| | |
|---|---|
| ***C08G 18/76*** | (2006.01) |
| ***C07C 263/20*** | (2006.01) |
| ***C07C 265/14*** | (2006.01) |
| ***C08G 18/10*** | (2006.01) |
| ***C08G 18/38*** | (2006.01) |
| ***C08G 18/64*** | (2006.01) |
| ***C08G 18/70*** | (2006.01) |
| ***C08G 18/71*** | (2006.01) |
| ***G02B 1/04*** | (2006.01) |

(52) U.S. Cl.

CPC ........ *C08G 18/7642* (2013.01); *C07C 263/20* (2013.01); *C07C 265/14* (2013.01); *C08G 18/10* (2013.01); *C08G 18/38* (2013.01); *C08G 18/3855* (2013.01); *C08G 18/3876* (2013.01); *C08G 18/64* (2013.01); *C08G 18/6453* (2013.01); *C08G 18/70* (2013.01); *C08G 18/71* (2013.01); *C08G 18/712* (2013.01); *C08G 18/76* (2013.01); *G02B 1/041* (2013.01)

(58) Field of Classification Search

CPC ........... C08G 18/7642; C08G 18/3876; C08G 18/712; C08G 18/70; C08G 18/10; C08G 18/38; C08G 18/64; C08G 18/71; C08G 18/76; C08G 18/3855; C08G 18/6453; C07C 263/20; C07C 265/14; G01B 1/041; G02B 1/041

See application file for complete search history.

(56) References Cited

U.S. PATENT DOCUMENTS

| | | | |
|---|---|---|---|
| 3,523,106 | A | 8/1970 | Davison |
| 3,799,963 | A | 3/1974 | Adams et al. |
| 2020/0190249 | A1 | 6/2020 | Yamasaki et al. |

FOREIGN PATENT DOCUMENTS

| | | | | | |
|---|---|---|---|---|---|
| CN | 109748822 | A | | 5/2019 | |
| CN | 112920374 | A | | 6/2021 | |
| EP | 3440053 | B1 | * | 9/2023 | ........... B01D 61/362 |
| EP | 3831806 | B1 | | 7/2024 | |
| JP | 05058982 | A | * | 3/1993 | |
| JP | 2006273717 | A | * | 10/2006 | |
| JP | 2019510789 | A | * | 4/2019 | ........... C07C 263/20 |
| JP | 2020-503325 | A | | 1/2020 | |
| KR | 19970001071 | A | | 1/1997 | |
| KR | 10-2008-0015515 | A | | 2/2008 | |
| KR | 10-0953019 | B1 | | 4/2010 | |
| KR | 10-1142576 | B1 | | 5/2012 | |
| KR | 10-2012-0076329 | A | | 7/2012 | |
| KR | 20180059520 | A | | 6/2018 | |
| KR | 10-2018-0104330 | A | | 9/2018 | |
| KR | 20180127517 | A | | 11/2018 | |
| KR | 20180133855 | A | | 12/2018 | |
| KR | 10-2019-0129819 | A | | 11/2019 | |
| KR | 10-2107329 | B1 | | 5/2020 | |
| WO | WO-2017174765 | A1 | * | 10/2017 | ........... C07C 263/20 |

OTHER PUBLICATIONS

Extended European Search Report for the European Patent Application No. 21900959.4 issued by the European Patent Office on Dec. 16, 2024.

Extended European Search Report for European Patent Application No. 21900959.4 issued by the European Patent Office on Apr. 24, 2025.

Notice of Allowance for the Korean Patent Application No. 10-2020-0167728 issued by the Korean Patent Office on Aug. 25, 2023.

Office Action for Chinese Patent Application No. 202180081127.9 issued by the Chinese Patent Office on May 31, 2025.

(Continued)

*Primary Examiner* — Rabon A Sergent

(74) *Attorney, Agent, or Firm* — IP & T GROUP LLP

(57) ABSTRACT

A xylylene diisocyanate composition according to exemplary embodiments includes xylylene diisocyanate (XDI) and chloromethylbenzyl isocyanate (CBI), and may satisfy a predetermined relationship between an acidity and a content of CBI. Thereby, an optical lens having a high transmittance and improved optical uniformity can be manufactured by controlling a polymerization reaction rate.

7 Claims, No Drawings

(56) References Cited

OTHER PUBLICATIONS

Office Action for the Korean Patent Application No. 10-2020-0167728 issued by the Korean Intellectual Property Office on Jul. 19, 2022.
International Search Report for the International Application No. PCT/KR2021/017850 issued by the International Searching Authority on Mar. 7, 2022.

* cited by examiner

XYLYLENE DIISOCYANATE COMPOSITION AND OPTICAL COMPOSITION COMPRISING SAME

This application is a national stage application of PCT/KR2021/017850 filed on Nov. 30, 2021, which claims priority to Korean Patent Application No. 10-2020-0167728 filed on Dec. 3, 2020. The disclosure of each of the foregoing applications is incorporated herein by reference in its entirety.

BACKGROUND

1. Field

The present invention relates to a xylylene diisocyanate composition and an optical composition including the same. More specifically, the present invention relates to a xylylene diisocyanate composition prepared through a reaction of an amine salt, and an optical composition including the same.

2. Description of the Related Art

A diisocyanate compound is widely used as, for example, a raw material for preparation of a polyurethane resin. For example, a diisocyanate compound is used to manufacture an optical lens using a polyurethane resin, and physical properties of the diisocyanate compound as a raw material for production thereof may directly affect optical properties such as transparency and refractive index of the optical lens.

For example, a polythiourethane resin prepared by reacting a polythiol compound and a diisocyanate compound may be used as a base material of the optical lens.

Among the diisocyanate compounds, xylylene diisocyanate (XDI) is widely used in consideration of chemical and optical properties such as reactivity and transparency.

For example, a polymerizable composition for an optical lens may be produced by preparing a composition including XDI and mixing it with a composition including a polythiol compound. In consideration of the stability of XDI and appropriate reactivity with the polythiol compound, it is necessary to design physical properties of the composition of XDI, the synthesis process and the like.

For example, Korean Patent Laid-Open Publication No. 2012-0076329 discloses a urethane-based optical material prepared using an isocyanate compound. However, the physical properties of the isocyanate composition itself are not considered.

SUMMARY

An object according to the exemplary embodiments is to provide a xylylene diisocyanate composition having improved reaction stability and optical properties.

An object according to exemplary embodiments is to provide an optical composition including a xylylene diisocyanate composition which has improved reaction stability and optical properties.

According to an aspect of the present invention, there is provided a xylylene diisocyanate composition including xylylene diisocyanate (XDI) and chloromethylbenzyl isocyanate (CBI), and satisfying Equation 1 below:

$$400 \leq \sqrt{\left(\frac{A}{2}\right)^2 + (2 \times B)^2} \leq 750 \quad \text{[Equation 1]}$$

in Equation 1, "A" is a content value of CBI in the XDI composition converted to ppm, "B" is an acidity value of the XDI composition converted to ppm, and A and B respectively represent numerical values in which the ppm unit is omitted.

In some embodiments, a content of chloromethylbenzyl isocyanate may range from 600 to 1,000 ppm based on a total weight of the composition.

In some embodiments, the xylylene diisocyanate composition may include an acidity regulator.

In some embodiments, the xylylene diisocyanate composition may have an acidity in a range of 100 to 350 ppm.

According to another aspect of the present invention, there is provided an optical composition including: a xylylene diisocyanate composition, which includes xylylene diisocyanate (XDI) and chloromethylbenzyl isocyanate (CBI), and satisfies Equation 1 below; and a polythiol-based compound:

$$400 \leq \sqrt{\left(\frac{A}{2}\right)^2 + (2 \times B)^2} \leq 750 \quad \text{[Equation 1]}$$

in Equation 1, "A" is a content value of CBI in the XDI composition converted to ppm, "B" is an acidity value of the XDI composition converted to ppm, and A and B respectively represent numerical values in which the ppm unit is omitted.

In some embodiments, the optical composition may further include an additive which includes at least one selected from the group consisting of a release agent, a reaction catalyst, a thermal stabilizer, an ultraviolet absorber and a bluing agent.

According to another aspect of the present invention, there is provided an optical product, including: a polythiourethane resin prepared from the polymerizable composition.

According to another aspect of the present invention, there is provided a method for preparing a xylylene diisocyanate composition, including: synthesizing xylylene diisocyanate from xylylene diamine to form a preliminary composition including xylylene diisocyanate; and adjusting a content of chloromethylbenzyl isocyanate (CBI) and an acidity in the preliminary composition by a distillation process at a temperature of 110 to 135° C.

In some embodiments, the step of adjusting the acidity in the preliminary composition may include introducing imidazole in a range of 200 to 1,000 ppm during the distillation process.

In some embodiments, the step of adjusting the content of chloromethylbenzyl isocyanate (CBI) and the acidity in the preliminary composition may include controlling the distillation process so as to satisfy Equation 1 below:

$$400 \leq \sqrt{\left(\frac{A}{2}\right)^2 + (2 \times B)^2} \leq 750 \quad \text{[Equation 1]}$$

in Equation 1, "A" is a content value of CBI in the XDI composition converted to ppm, "B" is an acidity value of the XDI composition converted to ppm, and A and B respectively represent numerical values in which the ppm unit is omitted.

According to the above-described embodiments, the xylylene diisocyanate composition satisfies a predetermined relationship between an acidity and a content of chloromethylbenzyl isocyanate (CBI), so as to provide improved stability and an appropriate range of polymerization reaction rate with the polythiol-based compound.

Accordingly, an optical lens having a high transmittance and improved optical uniformity from which white turbidity and inhomogeneity ("stria") phenomena are substantially removed can be manufactured.

DETAILED DESCRIPTION OF THE EMBODIMENTS

Hereinafter, embodiments of the present application will be described in detail. In this regard, the present invention may be altered in various ways and have various embodiments, such that specific embodiments will be illustrated in the drawings and described in detail in the present disclosure. However, the present invention is not limited to the specific embodiments, and it will be understood by those skilled in the art that the present invention is to cover all modifications, equivalents, and alternatives falling within the spirit and scope of the present invention.

Unless otherwise defined, all terms including technical and scientific terms used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

According to an aspect of the present invention, there is provided a composition including xylylene diisocyanate (XDI) (hereinafter, may be abbreviated as an XDI composition).

According to exemplary embodiments, the XDI composition may include XDI, and further include chloromethylbenzyl isocyanate (CBI).

CBI may be included in the XDI composition in a small amount to improve the stability of the composition, and may also function as a compound to regulate the reaction rate.

In some embodiments, a content of CBI in the XDI composition may be in a range of about 600 to 1000 ppm. Within the above range, stria and white turbidity phenomena of the XDI composition or an optical lens manufactured therefrom may be effectively suppressed, while suppressing an excessive decrease in the reaction rate of the XDI composition.

In a preferred embodiment, the content of CBI in the XDI composition may be in a range of about 600 to 800 ppm. More preferably, the content of CBI in the XDI composition may be in a range of 650 to 800 ppm, or 650 to 750 ppm.

CBI is generated together in the production or synthesis of the xylylene diisocyanate composition to be described below and may be included in the XDI composition. As will be described below, in one embodiment, the content of CBI may be adjusted through temperature control in a distillation process.

For example, CBI may include orthochloromethylbenzyl isocyanate, metachloromethylbenzyl isocyanate, parachloromethylbenzyl isocyanate. These may be included in the XDI composition alone or in combination of two or more thereof.

According to exemplary embodiments, in addition to the CBI content of the XDI composition, acidity may also be controlled so that, for example, optical and chemical stabilities of the composition and the reactivity with a polythiol-based compound may be regulated.

The term "acidity" as used herein may be a value expressed as a ratio of the amount of an acid component freed by a reaction with alcohol at room temperature based on a total weight of XDI, for example, in terms of HCl. For example, the acidity may be expressed in ppm.

According to exemplary embodiments, the XDI composition may satisfy Equation 1 below.

$$400 \leq \sqrt{\left(\frac{A}{2}\right)^2 + (2 \times B)^2} \leq 750 \qquad \text{[Equation 1]}$$

In Equation 1, "A" represents a content of CBI in the XDI composition, and "B" represents an acidity of the XDI composition. A and B illustrated in Equation 1 are used as numerical values omitting the unit (ppm).

For example, when the acidity of the XDI composition is too low, the reactivity with the polythiol-based compound may be excessively increased. Accordingly, instead of the desired polythiourethane resin, for example, other by-products in the form of oligomers or polymers may be increased, and optical non-uniformity of the lens may be increased to cause stria. Further, the self-reactivity of XDI is also increased, which may cause white turbidity phenomenon during long-term storage.

When the acidity of the XDI composition is excessively increased, the reactivity with the polythiol-based compound may decrease. Accordingly, the process yield of the polythiourethane resin for manufacturing the optical lens may be reduced. Further, white turbidity or yellowing phenomenon may result in the molded lenses.

According to exemplary embodiments, the content of CBI may be considered together as a buffering factor of acidity. For example, if the acidity of the XDI composition is excessively increased, the content of CBI may be decreased. When the acidity of the XDI composition is too low, the content of CBI may be relatively increased.

Therefore, by averaging the acidity and the CBI content, it is possible to maintain an appropriate reaction rate by adjusting the range defined in Equation 1. Accordingly, it is possible to obtain an optical product that suppresses the generation of by-products such as oligomers and prevents stria/white turbidity together. Further, long-term stability of the composition may also be secured.

According to exemplary embodiments, the reactivity or reaction rate factor may be adjusted by weighting the content of CBI indicated by A and the acidity of the XDI composition indicated by B. For example, as shown in Equation 1, it may be managed by giving an increased weight compared to the CBI content to the acidity, which is more sensitive to the physical properties of the polymerizable optical composition or optical product such as a lens.

Therefore, a more effective and precise suppression of by-product generation and the effect of controlling the reaction rate may be implemented.

In a preferred embodiment, the value according to Equation 1 is greater than 400 and may be less than 600. More preferably, the value according to Equation 1 may be 410 to 580, or 430 to 580.

As described above, according to exemplary embodiments, desired lens properties may be more finely and stably regulated by considering both the CBI content and acidity as reactivity/stability control factors of the XDI composition.

For example, even if the CBI content is in the range of about 600 to 1000 ppm as described above, when the acidity is too high or low, it may deviate from the range defined in Equation 1.

Further, in one example, when the acidity is too high, the content of CBI may be controlled to be low and adjusted to the range defined in Equation 1. In one example, when the acidity is too low, the CBI content may be controlled to be high and adjusted to the range defined in Equation 1.

Accordingly, as the CBI content and acidity are controlled together complementary to each other, deterioration in the physical properties of the optical lens due to any one of the CBI content and acidity may be inhibited.

In one embodiment, the acidity of the XDI composition may be adjusted in a range of about 100 to 350 ppm. Preferably, the acidity of the XDI composition may range from 100 to 250 ppm, and more preferably 110 to 230 ppm.

In some embodiments, an acidity regulator may be used to adjust the acidity of the XDI composition. For example, the acidity of the XDI composition may be adjusted to satisfy the range of Equation 1 by introducing the acidity regulator during the distillation process to be described below.

The acidity regulator may include an inorganic acid compound, an organic acid compound or a solid acid.

Examples of the inorganic acid compound may include halogen acids such as hydrochloric acid, hydrobromic acid, iodic acid, etc., sulfuric acid, phosphoric acid, phosphoric acid-based derivatives, or Lewis acids such as $SOCl_2$ or $SO_2Cl_2$ capable of releasing chlorine ions.

In an embodiment, the phosphoric acid-based derivative may include a phosphoric acid ester-based compound such as a phosphate-based compound or a phosphonate-based compound. For example, the phosphoric acid-based derivative may include a compound of Formula 1 below.

[Formula 1]

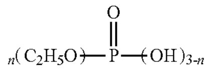

In Formula 1, n is 1 or 2.

Examples of the organic acid compound may include acetic acid, benzoic acid, formic acid, trifluoroacetic acid (TFA), fatty acid, aliphatic or cycloaliphatic carboxylic acid halide (such as acetyl chloride, trichloroacetyl chloride or N-chloroacetamide or N-bromosuccinimide); aromatic carboxylic acid halides (e.g., benzoyl chloride, phthaloyl chloride, terephthaloyl dichloride, isophthaloyl dichloride); aromatic, aliphatic or cycloaliphatic carbamyl chloride (e.g., N-phenylcarbamyl chloride, tert-butylcarbamyl chloride); acidic chlorosilane compounds (e.g., trimethylsilyl chloride, trimethylsilyl trifluoromethanesulfonate); sulfonic acid halides (e.g., tosyl chloride) and the like.

Examples of the solid acid may include acid clay, silica alumina, a cation exchange resin, acid-adhered silica gel, or a solid acid such as alumina, aluminum oxide, or vanadium oxide.

In some embodiments, the acidity regulator may include a basic compound that is not substantially reactive with XDI. For example, the acidity regulator may include a cyclic amine such as imidazole, tetrazole, pyridine, or the like, or a tertiary amine such as N,N-dimethylaniline (PhNMe2), triethylamine, trimethylamine and the like.

In one embodiment, the XDI content in the XDI composition may be 90% by weight ("wt. %") or more, 95 wt. % or more, or 99 wt. % or more, for example, may be 99 wt. % or more to less than 100 wt. %.

According to another aspect of the present invention, there is provided a method for preparing an XDI composition.

For example, xylylene diisocyanate (XDI) included in the XDI composition may be synthesized from xylylene diamine.

In some embodiments, XDI may be synthesized from xylylenediamine through a phosgene method. For example, xylylenediamine may be reacted with concentrated hydrochloric acid in a solvent to form an amine salt. XDI may be synthesized by reacting the amine salt with phosgene ($COCl_2$) (see Scheme 1 below).

[Scheme 1]

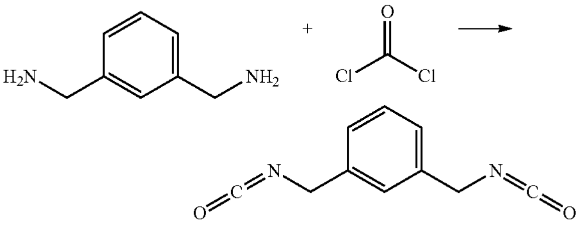

In some embodiments, XDI may be synthesized from xylylenediamine through a biphosgene method. For example, xylylenediamine may be reacted with concentrated hydrochloric acid to form an amine salt. The amine salt may be reacted with a halodialkyl carbonate to form a biscarbamate. XDI may be synthesized by thermally decomposing or degassing the biscarbamate in the presence of a catalyst (see Scheme 2 below).

[Scheme 2]

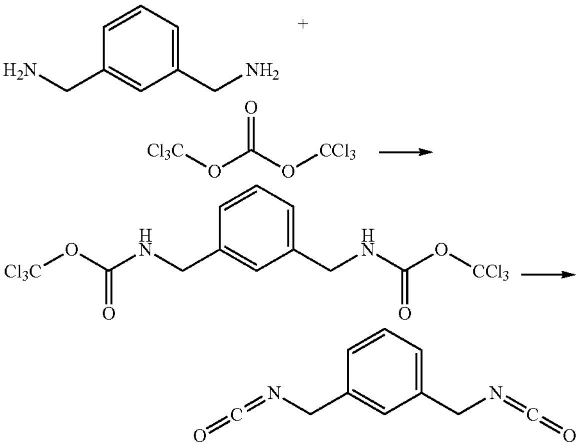

As shown in Scheme 2, bis(trichloromethyl)carbonate (BTMC) may be used as an example of the halodialkyl carbonate.

For example, a first solution in which the amine salt is dissolved in an inert solvent may be prepared, and a second solution in which the halodialkyl carbonate is dissolved in an inert solvent may be prepared. A biscarbamate synthesis reaction may be performed while the second solution is added dropwise to the first solution into a reactor. A temperature in the reactor may be maintained, for example, in a range of about 120 to 150° C., and preferably 120 to 140° C.

After completion of the dropping, a reaction may be performed while stirring the mixture for about 1 to 8 hours, or 2 to 6 hours, and preferably 3 to 5 hours.

Thereafter, a degassing process may be performed by supplying an inert gas to the reaction solution while maintaining the temperature in the above range. Then, the reaction solution may be cooled, and a preliminary XDI composition may be obtained through filtration and drying processes.

For example, after degassing, the reaction solution may be cooled to about 5 to 20° C., preferably about 10 to 20° C., and more preferably about 10 to 15° C. Thereafter, the preliminary XDI composition may be filtered using a ceramic filter such as a Celite-based filter.

In some embodiments, a distillation process may be further performed to remove the inert solvent and take out XDI. For example, a first distillation for removing the inert solvent and a second distillation for taking out XDI may be sequentially performed.

A first distillation temperature may be appropriately adjusted depending on the boiling point of the inert solvent. The second distillation may be performed at a second distillation temperature greater than or equal to the boiling point of XDI.

The inert solvent may include an organic solvent that is not substantially reactive with the amine salt, XDI, and the halodialkyl carbonate. Further, an organic solvent having a lower boiling point than XDI may be used for performing the above-described distillation process.

In one embodiment, the inert solvent may include a chlorinated aromatic hydrocarbon, for example, monochlorobenzene, dichlorobenzene, trichlorobenzene, chloroethylbenzene and the like.

For example, the first distillation temperature may be 40 to 80° C., preferably 50 to 70° C., and more preferably 55 to 65° C.

In exemplary embodiments, the content of CBI in the XDI composition may be adjusted to the above-described range by controlling the temperature of the distillation process.

In some embodiments, the second distillation temperature may be adjusted in the range of 110 to 135° C. For example, XDI extraction or purification may be sufficiently performed within the second distillation temperature range, and an excessive increase of the CBI content (e.g., more than 1,000 ppm) may be prevented. Preferably, the second distillation temperature may be 110 to 130° C., and more preferably 110 to 120° C.

According to exemplary embodiments, the above-described acidity regulator may be added in the distillation process. For example, the acidity of the preliminary XDI composition prepared as described above is measured and, when it is beyond the range defined in Equation 1, the acidity regulator may be added during the second distillation process.

When the value of Equation 1 of the preliminary XDI composition is less than 400, an acidic acidity regulator may be added. The acidity regulator may include the above-described inorganic acid compound, organic acid compound, or solid acid. Preferably, in consideration of fine acidity regulation, a liquid organic acid compound may be used.

When the value of Equation 1 of the preliminary XDI composition exceeds 750, the above-described basic compound such as imidazole may be added.

In a preferred embodiment, imidazole may be used as the acidity regulator. In some embodiments, an introduction amount of imidazole may be about 500 to 10,000 ppm of the preliminary XDI composition.

Within the above range, an appropriate acidity and reactivity of the XDI composition may be easily maintained. Accordingly, lens white turbidity due to excessively high acidity, or stria and chemical instability due to excessively low acidity may be inhibited.

Further, according to another aspect of the present invention, there is provided an optical composition (e.g., an optically polymerizable composition) including the XDI composition prepared as described above.

The polymerizable composition may include a polythiol-based compound and the XDI composition.

The polythiol-based compound may include a trifunctional polythiol compound and/or a tetrafunctional polythiol compound.

A non-limiting example of the trifunctional polythiol compound may include a compound represented by Formula 1 below.

[Formula 1]

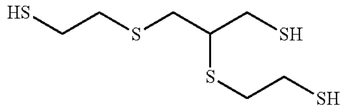

The trifunctional polythiol compound may be synthesized from, for example, a polyol compound obtained through a reaction with 2-mercaptoethanol and epihalohydrin.

After the polyol compound is reacted with thiourea under acidic conditions to produce a thiuronium salt, a trifunctional polythiol compound may be prepared through hydrolysis under basic conditions.

Non-limiting examples of the tetrafunctional polythiol compound may include compounds represented by Formulae 2-1 to 2-3 below.

[Formula 2-1]

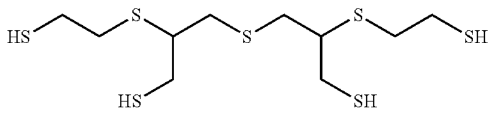

[Formula 2-2]

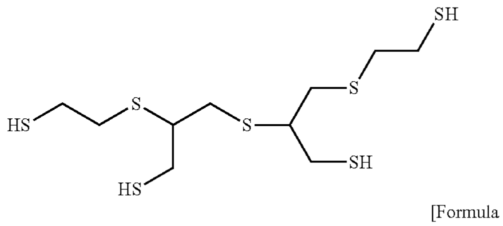

[Formula 2-3]

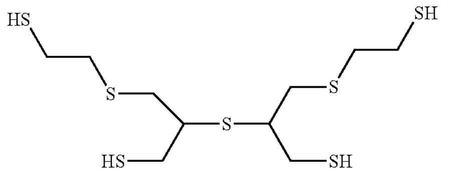

The tetrafunctional polythiol compound may be synthesized from, for example, a polyol compound obtained through a reaction with 2-mercaptoethanol and epihalohydrin. The polyol compound may be reacted with a metal sulfide to produce a tetrafunctional polyol intermediate. After the tetrafunctional polyol intermediate is reacted with thiourea under acidic conditions to produce a thiuronium salt, a tetrafunctional polythiol compound may be prepared by hydrolysis under basic conditions.

The optical composition may further include additives such as a release agent, a reaction catalyst, a thermal stabilizer, an ultraviolet absorber, a bluing agent and the like.

Examples of the release agent may include a fluorine-based nonionic surfactant having a perfluoroalkyl group, a hydroxyalkyl group or a phosphoric acid ester group; a silicone-based nonionic surfactant having a dimethylpolysiloxane group, a hydroxyalkyl group or a phosphoric acid ester group; alkyl quaternary ammonium salts such as trimethylcetyl ammonium salt, trimethylstearyl, dimethylethylcetyl ammonium salt, triethyldodecyl ammonium salt, trioctylmethyl ammonium salt and diethylcyclohexadodecyl ammonium salt; acidic phosphoric acid ester and the like. These may be used alone or in combination of two or more thereof.

As the reaction catalyst, a catalyst used in the polymerization reaction of the polythiourethane resin may be used. For example, dialkyltin halide catalysts, such as dibutyltin dichloride and dimethyltin dichloride; dialkyltin dicarboxylate catalysts such as dimethyltin diacetate, dibutyltin dioctanoate, and dibutyltin dilaurate; dialkyltin dialkoxide catalysts such as dibutyltin dibutoxide and dioctyltin dibutoxide; dialkyltin dithio alkoxide catalysts such as dibutyltin di(thiobutoxide); dialkyltin oxide catalysts such as di(2-ethylhexyl)tin oxide, dioctyltin oxide, and bis(butoxydibutyltin) oxide; dialkyltin sulfide catalysts, and the like may be used. These may be used alone or in combination of two or more thereof.

As examples of the ultraviolet absorber, benzophenone-based, benzotriazole-based, salicylate-based, cyanoacrylate-based, oxanilide-based compounds, and the like may be used. As examples of the thermal stabilizer, metal fatty acid salt-based, phosphorus-based, lead-based, organotin-based compounds, and the like may be used. These may be used alone or in combination of two or more thereof.

The bluing agent may be included as a color regulator of the optical material prepared from the polythiourethane resin. For example, the bluing agent may have an absorption band in a wavelength band from orange to yellow in a visible light region.

Examples of the bluing agent may include a dye, a fluorescent whitening agent, a fluorescent pigment, an inorganic pigment, and the like, and may be appropriately selected according to physical properties or resin color required for the optical product to be manufactured. When the dye is used as the bluing agent, for example, a dye having a maximum absorption wavelength of 520 to 600 nm, and preferably 540 to 580 nm may be used. Preferably, anthraquinone-based dyes may be used.

In some embodiments, the polythiol-based compound may be included in an amount of about 40 to 60 wt. %, the isocyanate-based compound may be included in an amount of about 40 to 60 wt. %, and the additive may be included in an amount of about 0.01 to 1 wt. %, based on the total weight of the optical composition.

The polythiourethane resin may be produced through a polymerization reaction of the polythiol-based compound and XDI included in the optical composition.

As described above, the XDI composition used in the optical composition may be regulated to satisfy Equation 1 so as to appropriately control the reactivity or reaction rate with the polythiol-based compound. Accordingly, while suppressing a white turbidity phenomenon derived from the XDI composition itself, the white turbidity phenomenon in the optical lens manufactured using the optical composition may also be prevented.

Further, through stable polymerization reaction, an optical lens having uniform refractive index without stria phenomenon may be produced.

In some embodiments, the reaction rate of the optical composition included in Equation 1 to be described below may be regulated to 0.15 to 0.23, preferably maintained to 0.18 to 0.23, and more preferably 0.20 to 0.23, or 0.21 to 0.23.

Furthermore, according to another aspect of the present invention, an optical product manufactured through the above-described optical composition may be provided.

For example, after degassing the optical composition under reduced pressure, the resultant product may be injected into a mold for molding an optical material. Injection into the mold may be performed, for example, in a temperature range of 20 to 40° C.

After the injection into the mold, the temperature may be gradually increased, thereby allowing a polymerization reaction of the polythiourethane resin to proceed. The polymerization temperature may be 20 to 150° C., and preferably 25 to 130° C.

The polymerization temperature may be 20 to 150° C., and preferably 25 to 130° C. For example, the maximum polymerization temperature may range from 100 to 150° C., preferably 110 to 140° C., and more preferably 115 to 130° C.

The heating rate may be 1 to 10° C./min, preferably 3 to 8° C./min, and more preferably 4 to 7° C./min. The polymerization time may be 10 to 20 hours, and preferably to 20 hours.

After polymerization, the polymerized polythiourethane resin may be separated from the mold to obtain an optical product. In one embodiment, after separation from the mold, a curing process may be further conducted. The curing process may be conducted in a range of 100 to 150° C., preferably 110 to 140° C., and more preferably 115 to 130° C. for about 1 to 10 hours, preferably 2 to 8 hours, and more preferably 2 to 6 hours.

The optical product may be manufactured in the form of a spectacle lens, a camera lens, a light emitting diode, etc. according to a shape of the mold.

The refractive index of the optical product may be adjusted according to the type and/or content ratio of the polythiol-based compound and the isocyanate-based compound used in the polymerizable composition for an optical material. For example, the refractive index of the optical product may be adjusted in a range of 1.56 to 1.78, 1.58 to 1.76, 1.60 to 1.78, or 1.60 to 1.76, and preferably in a range of 1.65 to 1.75 or 1.69 to 1.75.

The optical product may be improved by further conducting surface treatment such as anti-fouling, color imparting, hard coat, surface polishing, hardness strengthening and the like.

Hereinafter, embodiments provided in the present application will be further described with reference to specific experimental examples. However, the following experimental examples only illustrate the present invention and are not intended to limit the appended claims, and those skilled in the art will obviously understand that various alterations and modifications are possible within the scope and spirit of the present invention. Such alterations and modifications are duly included in the appended claims.

Example 1

(1) Preparation of Xylylenediamine (XDA) Hydrochloric Acid Salt 1009.4 g (9.46 mol) of a 35% hydrochloric acid solution was introduced into a reactor, and the reactor was cooled to decrease an internal temperature to a range of 15 to 20° C. while stirring. Then, 600.0 g (4.4 mol) of meta-xylylenediamine (m-XDA) was slowly introduced while maintaining the reactor temperature in a range of 20 to 60° C.

After introduction of m-XDA, the reactor was cooled to decrease the internal temperature to a range of 10 to 20° C. and, after stirring for 1 hour, 1,320.0 g of tetrahydrofuran was added. Then, the reactor was cooled again to decrease the internal temperature to a range of −5 to 0° C., and the reaction was allowed to proceed along with additional stirring for 1 hour.

After termination of the reaction, vacuum filtration was conducted, followed by drying at an external temperature outside the reactor in a range of 90 to 100° C. and under a condition of a vacuum pump of 0.1 torr to remove residual solvent and moisture, thereby obtaining m-XDA hydrochloride.

(2) Preparation of Xylylene Diisocyanate Composition 800 g of m-XDA hydrochloride prepared in the above (1) and 3,550 g of ortho-diclobenzene (ODCB) were introduced into the reactor, and the reactor was heated to increase the internal temperature to about 125° C. while stirring.

950 g of bis(trichloromethyl) carbonate (BTMC) and 800 g of ODCB were dissolved while stirring at about 60° C., and then the reactor temperature was dropped to 125° C. over 24 hours so as to prevent precipitation. After completion of dropping, pre-mixing was conducted for 4 hours.

After termination of the reaction, $N_2$ gas was fed to the reaction solution at a temperature of 125° C., followed by a degassing process while bubbling. After the degassing reaction solution was cooled to 10° C., the remaining solids were filtered using Celite 545.

The filtered organic solvent and the synthesized crude XDI were purified by distillation under the following conditions. During the second distillation process, 2,000 ppm of imidazole was introduced.

1) Removal of Organic Solvent (ODCB) (First Distillation)
   Vacuum: 0.5 torr or less
   Distillation column bottom temperature: 60° C.
   Distillation time: 8 hours 2) XDI Distillation (Second Distillation)
   Vacuum: 0.5 torr or less
   Distillation column bottom temperature: 120° C.
   Distillation time: 10 hours (3) Preparation of Polymerizable Composition for an Optical Material and Lens 49.3 parts by weight ("wt. parts") of 4,8-bis(mercaptomethyl)-3,6,9-trithiaundecane-1,11-dithiol as a polythiol compound, 50.7 wt. parts of xylylene diisocyanate synthesized according to the above preparation, 0.01 wt. parts of dibutyltin chloride, and 0.1 wt. parts of phosphoric acid ester release agent produced by ZELEC® UN Stepan were uniformly mixed, followed by conducting a defoaming process at 600 Pa for 1 hour, thereby preparing a polymerizable composition for an optical material.

The resin composition filtered through a 3 μm Teflon filter was injected into a mold including a glass mold and a tape. After maintaining the mold at 10 to 25° C. for 8 hours, the temperature was slowly increased to 130° C. for 8 hours at a constant rate, and polymerization was performed at 130° C. for 2 hours. After the polymerization was completed, the mold was separated and the product was further cured at 120° C. for 2 hours to produce a lens sample.

Examples 2-8 and Comparative Examples

XDI compositions and lens samples were prepared in the same manner as in Example 1, except that the distillation column bottom temperature and the imidazole addition amount in the second distillation process were changed as described in Table 1 below.

Experimental Example (1) Measurement of CBI Content

The XDI composition prepared as described above was analyzed by gas chromatography (GC) under the following conditions to measure the number of moles of chloromethylbenzyl isocyanate, and the content of CBI was measured through conversion thereof.

GC Measurement Conditions
   i) Equipment name: Agilent 6890/7890
   ii) Carrier gas: He
   iii) Injector: 250° C.
   iv) Oven temperature: 40 to 320° C.
   y) Column: HP-1, Wax, 30 m
   vi) Detector: FID, 300° C.

(2) Measurement of Acidity 20 g of the prepared XDI composition sample was quantified and introduced into a 200 ml beaker, 100 ml of a solvent (acetone and ethanol mixed in a 1:1 weight ratio) was added thereto and heated on a hot plate to dissolve the sample, followed by mixing the solution at room temperature for 10 to 20 minutes.

Then, using an automatic measurement device (Hiranuma COM-500), in accordance with JIS K4101, acidity was calculated according to the following equation, such that a solution (N/100 methanolic potassium hydroxide solution) prepared by diluting 0.1 mol/L methanolic potassium hydroxide adjusted and expressed using methanol was used to form a titration curve, and an increasing point of the curve was used as the endpoint.

$$\text{Acidity}=0.0365\times(A-B)\times f/S$$

A: Amount (ml) of 0.1 mol/L methanolic potassium hydroxide used in the actual titration B: Amount (ml) of 0.1 mol/L methanolic potassium hydroxide used for titration of the control measured without sample f: Correction factor of N/100 methanolic potassium hydroxide solution S: Weight (g) of introduced sample (3) Evaluation of White Turbidity of XDI Composition After storing the XDI compositions of the examples and comparative examples in a dark room at 25° C. for 3 months, the composition stock solution was visually observed and evaluated as follows.

○: Completely transparent
Δ: Partial haze observed
x: Complete haze was clearly observed (4) Assessment of Lens Properties 1) Evaluation of Stria As described above, a lens sample having a diameter of 75 mm and −4.00 D was prepared using the polymerizable composition according to each of the examples and comparative examples. A light from a mercury lamp light source was transmitted through the prepared lens sample, and the transmitted light was projected on a white plate to determine the presence or absence of stria according to the presence or absence of contrast. Standards for evaluation are as follows.

○: Stria not observed

Δ: Fine partial stria observed x: Stria clearly observed visually

2) Evaluation of White Turbidity of Lens

For the lens samples of the examples and comparative examples prepared as described above, each sample was irradiated with light beams from a projector in a dark room, and it was visually confirmed whether the lens had haze or an opaque material.

Standards for evaluation are as follows.

○: No haze

Δ: Partial haze observed x: Haze clearly observed as a whole

3) Measurement of Polymerization Reaction Rate (Reactivity Slope)

Using a non-contact viscometer of EMS-1000 (KEM), the standard viscosity (Standard cps) was first confirmed with a viscosity standard solution (Brookfield, 1000 cps, 25° C.). Thereafter, the viscosity was measured at 10° C. for 24 hours for the polymerizable compositions according to the examples and comparative examples, respectively. Using the measured values, mathematical formulation ("mathematization") was conducted with an X-axis as a time and a Y-axis as a viscosity while converting the Y-axis in a logarithmic scale as shown in Mathematical Equation 1 below, and then the reaction rate was derived therefrom.

$$Y = a \times \exp(b \times X) \quad \text{[Mathematical Equation 1]}$$

In Mathematical Equation 1, 'a' value represents an initial viscosity (cps) while 'b' value represents the reaction rate, the measured value was expressed by rounding to the two decimal places of the measured value.

4) Measurement of Color Index (Yellow Index (YI))

For lens samples of the examples and comparative examples manufactured in a plastic cylinder form (r (radius)×H (height)=16 mm×45 mm), light was transmitted in a height direction of the plastic cylinder to measure Y.I. through UV/VIS Spectroscopy (PerkinElmer, Model UV/VIS Lambda 365).

Specifically, Y.I was calculated by the following Equation (1) based on the values of x and y.

$$Y.I = (234 \times x + 106 \times y)/y \quad \text{[Equation (1)]}$$

Evaluation results are shown together in Tables 1 and 2 below.

TABLE 1

| | Second distillation temperature (° C.) | Introduced amount of imidazole (ppm) | CBI (ppm) | Acidity of XDI composition (ppm) | Value of Equation 1 |
|---|---|---|---|---|---|
| Example 1 | 120 | 2000 | 781 | 242 | 622 |
| Example 2 | 120 | 500 | 810 | 267 | 670 |
| Example 3 | 120 | 10000 | 724 | 124 | 439 |
| Example 4 | 110 | 2000 | 699 | 144 | 453 |
| Example 5 | 110 | 500 | 701 | 229 | 577 |
| Example 6 | 110 | 10000 | 687 | 115 | 413 |
| Example 7 | 135 | 500 | 825 | 308 | 741 |
| Example 8 | 135 | 10000 | 831 | 239 | 633 |
| Comparative Example 1 | 140 | 2000 | 1238 | 225 | 765 |
| Comparative Example 2 | 145 | 2000 | 1511 | 204 | 859 |
| Comparative Example 3 | 160 | 2000 | 1690 | 218 | 951 |
| Comparative Example 4 | 120 | 12000 | 787 | 24 | 396 |
| Comparative Example 5 | 120 | 15000 | 777 | 6 | 389 |
| Comparative Example 6 | 120 | 300 | 855 | 612 | 1297 |
| Comparative Example 7 | 120 | 0 | 859 | 668 | 1403 |
| Comparative Example 8 | 100 | 2000 | 535 | 1021 | 2059 |
| Comparative Example 9 | 80 | 2000 | 455 | 1211 | 2433 |

TABLE 1-continued

TABLE 2

| | White turbidity of composition | Physical properties of lens | | | |
|---|---|---|---|---|---|
| | | Stria | White turbidity | Reactivity, polymerization rate | Y.I |
| Example 1 | ○ | ○ | ○ | 0.21 | 21 |
| Example 2 | ○ | ○ | ○ | 0.22 | 22 |
| Example 3 | ○ | ○ | ○ | 0.23 | 21 |
| Example 4 | ○ | ○ | ○ | 0.23 | 20 |
| Example 5 | ○ | ○ | ○ | 0.22 | 20 |
| Example 6 | ○ | ○ | ○ | 0.23 | 20 |
| Example 7 | ○ | ○ | ○ | 0.21 | 23 |
| Example 8 | ○ | ○ | ○ | 0.22 | 23 |
| Comparative Example 1 | Δ | ○ | ○ | 0.24 | 25 |
| Comparative Example 2 | Δ | ○ | ○ | 0.26 | 26 |
| Comparative Example 3 | Δ | ○ | ○ | 0.27 | 26 |
| Comparative Example 4 | x | x | ○ | 0.30 | 23 |
| Comparative Example 5 | x | x | ○ | 0.31 | 22 |
| Comparative Example 6 | ○ | ○ | Δ | 0.14 | 26 |
| Comparative Example 7 | ○ | ○ | Δ | 0.14 | 26 |
| Comparative Example 8 | ○ | ○ | x | 0.12 | 27 |
| Comparative Example 9 | ○ | ○ | x | 0.12 | 27 |

Referring to Tables 1 and 2, in the examples in which the value of Equation 1 was adjusted in the range of 400 to 750 as described above, white turbidity in the composition and lens state was prevented, and an appropriate polymerization reaction rate was obtained.

On the other hand, in the case of Comparative Examples 4 and 5 in which the value of Formula 1 is less than 400, composition white turbidity and lens stria phenomena were observed due to excessive reactivity. Referring to Comparative Examples 1 to 3, when the value of Equation 1 exceeds 750, a yellowing phenomenon of the lens was caused. Referring to Comparative Examples 6 to 9, when the value of Equation 1 exceeds 1,000, the lens white turbidity phenomenon was caused. In addition, as the polymerization reaction rate was excessively decreased, the yield of the lens sample was decreased.

What is claimed is:

1. A xylylene diisocyanate composition, comprising xylylene diisocyanate (XDI) and chloromethylbenzyl isocyanate (CBI), and satisfying Equation 1 below, wherein a content of chloromethylbenzyl isocyanate ranges from 600 to 1,000 ppm based on a total weight of the composition, and wherein the xylylene diisocyanate composition has an acidity value in a range of 110 to 350 ppm, $$400 \le \sqrt{\left(\frac{A}{2}\right)^2 + (2 \times B)^2} \le 750, \quad \text{[Equation 1]}$$

in Equation 1, "A" is a content value of CBI in the XDI composition converted to ppm, "B" is an acidity value of the XDI composition converted to ppm, and A and B respectively represent numerical values in which the ppm unit is omitted.

2. The xylylene diisocyanate composition according to claim 1, further comprising an acidity regulator.

3. An optical composition comprising:

a xylylene diisocyanate composition comprising xylylene diisocyanate (XDI) and chloromethylbenzyl isocyanate (CBI), and satisfying Equation 1 below; and a polythiol-based compound, wherein a content of chloromethylbenzyl isocyanate ranges from 600 to 1,000 ppm based on a total weight of the composition, and wherein the xylylene diisocyanate composition has an acidity value in a range of 110 to 350 ppm, $$400 \le \sqrt{\left(\frac{A}{2}\right)^2 + (2 \times B)^2} \le 750, \quad \text{[Equation 1]}$$

in Equation 1, "A" is a content value of CBI in the XDI composition converted to ppm, "B" is an acidity value of the XDI composition converted to ppm, and A and B respectively represent numerical values in which the ppm unit is omitted.

4. The optical composition according to claim 3, further comprising an additive which includes at least one selected from the group consisting of a release agent, a reaction catalyst, a thermal stabilizer, an ultraviolet absorber and a bluing agent.

5. An optical product, comprising:

a copolymer of a xylylene diisocyanate composition and a polythiol-based compound, wherein the xylylene diisocyanate composition comprises xylylene diisocyanate (XDI) and chloromethylbenzyl isocyanate (CBI), and satisfies Equation 1 below, wherein a content of chloromethylbenzyl isocyanate ranges from 600 to 1,000 ppm based on a total weight of the composition, and wherein the xylylene diisocyanate composition has an acidity value in a range of 110 to 350 ppm, $$400 \le \sqrt{\left(\frac{A}{2}\right)^2 + (2 \times B)^2} \le 750, \quad \text{[Equation 1]}$$

(in Equation 1, "A" is a content value of CBI in the XDI composition converted to ppm, "B" is an acidity value of the XDI composition converted to ppm, and A and B respectively represent numerical values in which the ppm unit is omitted).

6. A method for preparing a xylylene diisocyanate composition, comprising:

synthesizing xylylene diisocyanate (XDI) from xylylene diamine to form a preliminary composition including xylylene diisocyanate; and adjusting a content of chloromethylbenzyl isocyanate (CBI) and an acidity in the preliminary composition by a distillation process at a temperature of 110 to 135° C., wherein the step of adjusting comprises controlling the distillation process so as to satisfy Equation 1 below, wherein a content of chloromethylbenzyl isocyanate ranges from 600 to 1,000 ppm based on a total weight of the composition, and wherein the xylylene diisocyanate composition has an acidity value in a range of 110 to 350 ppm, $$400 \le \sqrt{\left(\frac{A}{2}\right)^2 + (2 \times B)^2} \le 750, \quad \text{[Equation 1]}$$

in Equation 1, "A" is a content value of CBI in the XDI composition converted to ppm, "B" is the acidity value of the XDI composition converted to ppm, and A and B respectively represent numerical values in which the ppm unit is omitted.

7. The method according to claim 6, wherein the step of adjusting the acidity in the preliminary composition comprises introducing imidazole in a range of 500 to 10,000 ppm during the distillation process.

* * * * *